(12) United States Patent
Schmitt et al.

(10) Patent No.: US 10,010,513 B2
(45) Date of Patent: Jul. 3, 2018

(54) AQUEOUS PHARMACEUTICAL COMPOSITION CONTAINING A BIOLOGIC THERAPEUTIC AGENT AND GUANIDINE OR A GUANIDINE DERIVATIVE AND AN INJECTION INCLUDING THE COMPOSITION

(71) Applicant: Novartis AG, Basel (CH)

(72) Inventors: David Schmitt, Hirsingue (FR); Hans-Joachim Wallny, Grenzach-Wyhlen (DE)

(73) Assignee: Novartis AG, Basel (CH)

( * ) Notice: Subject to any disclaimer, the term of this patent is extended or adjusted under 35 U.S.C. 154(b) by 535 days.

(21) Appl. No.: 13/900,724

(22) Filed: May 23, 2013

(65) Prior Publication Data

US 2013/0317457 A1 Nov. 28, 2013

Related U.S. Application Data

(60) Provisional application No. 61/651,588, filed on May 25, 2012.

(51) Int. Cl.
| | | |
|---|---|---|
| *A61K 39/395* | (2006.01) | |
| *A61K 31/155* | (2006.01) | |
| *A61F 9/00* | (2006.01) | |
| *A61K 31/198* | (2006.01) | |
| *A61K 9/00* | (2006.01) | |
| *A61K 47/18* | (2017.01) | |
| *A61K 47/26* | (2006.01) | |
| *C07K 16/18* | (2006.01) | |

(52) U.S. Cl.
CPC .......... *A61K 31/155* (2013.01); *A61F 9/0008* (2013.01); *A61K 9/0051* (2013.01); *A61K 31/198* (2013.01); *A61K 39/395* (2013.01); *A61K 39/39591* (2013.01); *A61K 47/18* (2013.01); *A61K 47/183* (2013.01); *A61K 47/26* (2013.01); *C07K 16/18* (2013.01)

(58) Field of Classification Search
None
See application file for complete search history.

(56) References Cited

U.S. PATENT DOCUMENTS

| | | | | |
|---|---|---|---|---|
| 5,364,884 A | * | 11/1994 | Varma | A61K 31/16 514/551 |
| 5,658,948 A | * | 8/1997 | Lucero | A61K 9/0048 514/554 |
| 6,171,586 B1 | * | 1/2001 | Lam | A61K 39/39591 424/130.1 |
| 6,462,071 B1 | * | 10/2002 | Castillejos | A61K 31/17 514/413 |
| 2006/0182783 A1 | * | 8/2006 | Hughes | A61F 9/0008 424/427 |
| 2010/0034809 A1 | | 2/2010 | Diefenbach-Streiber et al. | |

FOREIGN PATENT DOCUMENTS

| | | |
|---|---|---|
| WO | 02/17831 A2 | 3/2002 |
| WO | 2004055164 A2 | 7/2004 |
| WO | 2008113834 A2 | 9/2008 |
| WO | 2011084750 A1 | 7/2011 |

OTHER PUBLICATIONS

Hrach, Charles et al., Retinal Toxicity of Commercial Intravitreal Tissue Plasminogen Activator Solution in Cat Eyes, Arch Ophthalmol, May 2000, pp. 659-663, vol. 118.
Johnson, Mark et al., Retinal Toxicity of Recombinant Tissue Plasminogen Activator in the Rabbit, Arch Ophthalmol, Feb. 1990, pp. 259-263, vol. 108.
Vogelson, Cullen et al., Preclinical and Clinical Antiallergic Effect of Olopatadine 0.2% Solution 24 Hours after Topical Ocular Administration, Allergy and Asthma Proc., Jan.-Feb. 2004, pp. 69-75, vol. 25-1.
Yanni, J. M. et al., The In Vitro and In Vivo Ocular Pharmacology of Olopatadine (AL-4943A), and Effective Anti-Allergic/ Antihistaminic Agent, Journal of Ocular Pharmacology and Therapeutics, 1996, pp. 1-12, vol. 12-4.
Shire, Steven et al., Challenges in the Development of High Protein Concentration Formulations, Current Trends in Monoclonal Antibody Development and Manufacturing, Jan. 1, 2010, pp. 131-147, vol. XI.
PCT International Search Report for corresponding PCT/EP2013/060649 dated Aug. 5, 2013.
L. Chang e t al: "Mechanism of protein stabilization by sugars during freeze-drying and storage: native structure preservation, specific interaction, and/or immobilization in a glassy matrix?", Journal of Pharmaceutical Sciences, vol. 94, No. 7 Jul. 2005, pp. 1427-1444.
Belikov V.G., Farmatsevticheskaya Khimiya (Pharmaceutical Chemistry), Moscow: Vysshaya Shkola, 1993, pp. 43-47.

* cited by examiner

*Primary Examiner* — Yunsoo Kim
(74) *Attorney, Agent, or Firm* — Jason J. Derry

(57) ABSTRACT

The present invention is directed to an aqueous pharmaceutical composition, particularly an aqueous ophthalmic composition, suitable as an injection, particularly an intravitreal injection. The composition includes a biologic therapeutic agent (e.g., an isolated monoclonal antibody that specifically binds to a C5 protein) that tends to raise the viscosity of the composition and a guanidine and/or guanidine derivative (e.g., L-arginine) that tends to lower the viscosity of the composition.

13 Claims, 1 Drawing Sheet

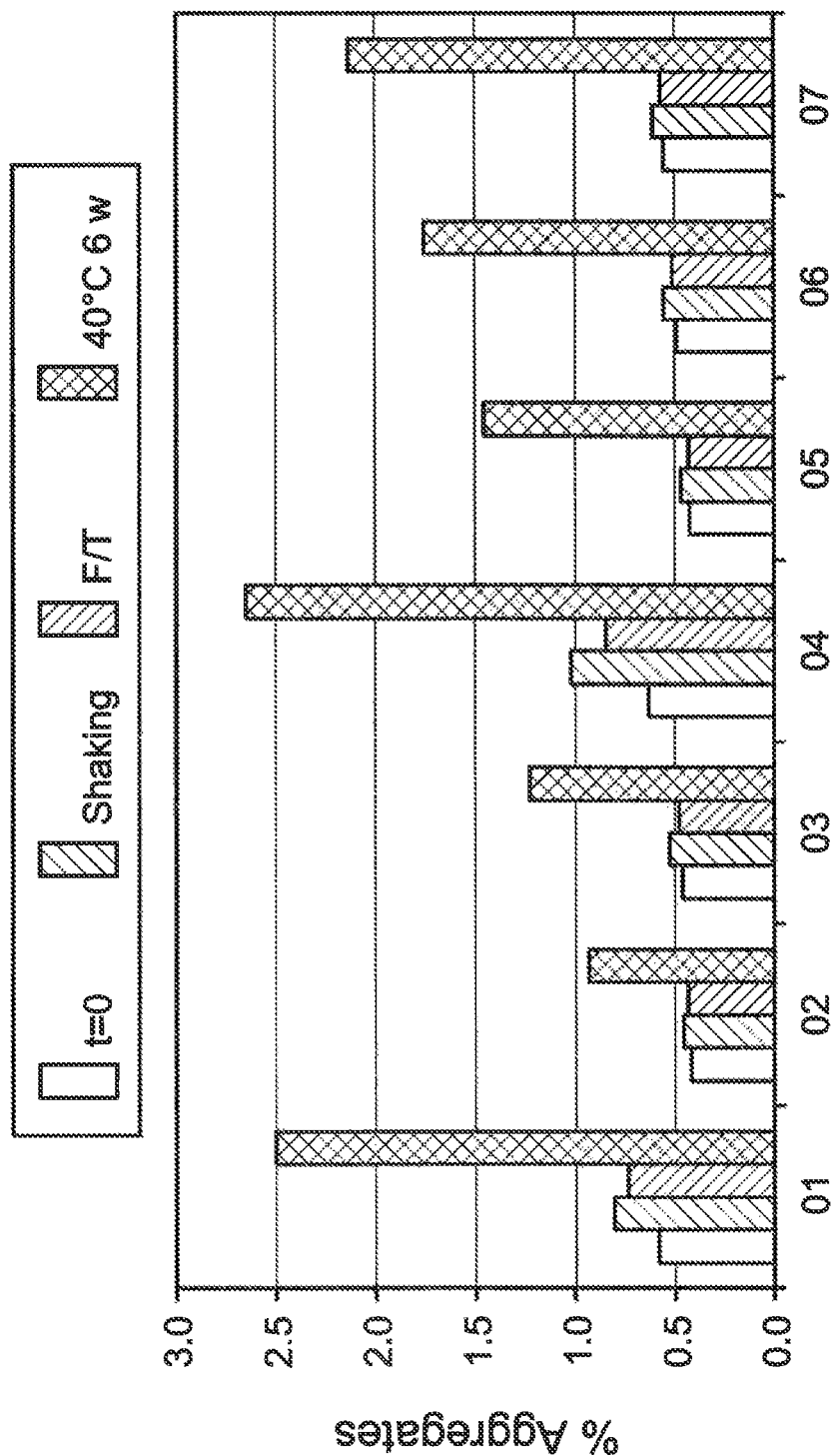

AQUEOUS PHARMACEUTICAL COMPOSITION CONTAINING A BIOLOGIC THERAPEUTIC AGENT AND GUANIDINE OR A GUANIDINE DERIVATIVE AND AN INJECTION INCLUDING THE COMPOSITION

CROSS-REFERENCE TO RELATED APPLICATION

The present application claims priority based on U.S. Provisional Patent Application Ser. No. 61/651,588 filed May 25, 2012.

TECHNICAL FIELD OF THE INVENTION

The present invention is related to an aqueous pharmaceutical composition, particularly an aqueous ophthalmic composition, suitable as an injection, particularly an intravitreal injection, the composition including a biologic therapeutic agent (e.g., an isolated monoclonal antibody that specifically binds to a C5 protein), and guanidine and/or a guanidine derivative (e.g., L-arginine).

BACKGROUND OF THE INVENTION

The pharmaceutical industry has been developing compositions that include biologic therapeutic agents (e.g., biologics such as monoclonal antibodies) for many years for the treatment of a variety of maladies. Such biologics tend to be relatively large molecules which are quite amenable to oral delivery and some forms of parenteral delivery. However, biologics can present drawbacks for delivery by injection, particularly intravitreal injection. Due to their size, biologics, when included in aqueous compositions, often impart substantial viscosity to those compositions. In turn, such compositions can be difficult to administer through an injection device (e.g., a syringe). However, injection of a biologic at a site of a disease or malady is quite desirable.

As a consequence, the pharmaceutical industry has committed substantial resources to developing techniques to lower the viscosity of aqueous compositions that include a biologic such as a monoclonal antibody. While the industry has been successful in its efforts to lower the viscosity of many aqueous composition containing biologics, forming a composition suitable for injection, particularly intravitreal injection, can be particularly daunting. For an intravitreal injection in particular, it is typically desirable to use a very small gauge needle (i.e., typically at least 28 gauge and more typically at least 30 gauge) to avoid harm to the eye. However, pushing a viscous composition through such a small needle is particularly undesirable since it can be difficult for doctors to determine a proper amount of force to use to deliver the composition at a desired rate.

Intravitreal injections are particularly desirable for treating retinal diseases such as age related macular degeneration (AMD) since an injection device (e.g., a syringe with a needle) is typically used to located the injections in the vitreous closer to the retina, which is located at the back of the eye. Recently, it has been is discovered that an IgG1/lambda isotype monoclonal antibody is able to slow the advance of age related macular degeneration (AMD), see U.S. Patent Application No. 20100034809, which is incorporated herein by reference for all purposes. Unfortunately, the IgG1/lambda isotype monoclonal antibody, like many such antibodies, tends to significantly raise the viscosity of an aqueous compositions making it difficult to deliver as an intravitreal injection.

One mechanism for lowering the viscosity of an aqueous composition containing monoclonal antibodies is to include some amount of one or more selected chemical compounds capable of causing a viscosity reduction. Arginine, particularly L-arginine, has been found to be particularly effective in lowering the viscosity of aqueous compositions. However, it has been suggested that arginine, particularly L-arginine, can be toxic to the eye and other human tissue. See: *Retinal Toxicity of Commercial Intravitreal Tissue Pasminogen Activator Solution in Cat Eyes*, Charles J Hrach, MD; Mark W. Johnson, MD; Adam S. Hassan, MD; Bo Lei, MD; Paul A. Sieving, MD, Phd; Victor M. Elner MD, PhD, *Arch Ophthalmol.* 2000; 118:659-663; and *Retinal Toxicity of Recombinant Tissue Pasminogen Activator in the Rabbit*, Mark W. Johnson, MD; Karl R. Olsen, MD; Eleut Hernandez; W. David Irvine, MD; Robert N. Johnson, MD, *Arch Ophthalmol.* 1990; 108(2):259-263. Consequently, the pharmaceutical community, particularly the ophthalmic community, has avoided use of compounds such as arginine, particularly L-arginine, in ophthalmic compositions for lowering viscosity.

Unexpectedly, however, the inventors of the composition of the present invention have discovered that a group of compounds and particularly arginine can be used at relatively low concentrations to lower the viscosity of aqueous compositions containing particular biologics such as monoclonal antibodies, particularly IgG1/lambda isotype monoclonal antibodies. Further, it has been found that viscosity can be lowered enough to be suitable for injection and even suitable for intravitreal injection without harming the retina or other ocular tissue.

SUMMARY OF THE INVENTION

Accordingly, the present invention is directed to an aqueous composition suitable for injection. The composition includes a biologic therapeutic agent, guanidine and/or guanidine derivative (e.g., guanidine only, guanidine derivative only or a combination thereof) and water. The biologic therapeutic agent, when is used to form a solution having a concentration of 100 mM of the biologic therapeutic agent in water, results in the solution having a viscosity that is at least 10 cp. The guanidine derivative has the following formula:

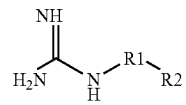

wherein:

R1 is nothing, $CH_3$, $C_nH_{2n+1}$, $C_nH_{2n}$, or $C_nH_{2n-1}$ (n=1-10); and/or R2 is nothing or any chemical group that does not significantly reduce the ability of the guanidinium group to lower the viscosity of the composition; and R1 and R2 are never nothing at the same time.

The guanidine and/or guanidine derivative is present in the composition at a concentration of at least 25 mM but no greater than 100 mM. Further, the composition has a viscosity that is no greater than 10 centipoise and more preferably no greater than 7 centipoise.

The composition is particularly desirable as an aqueous ophthalmic composition suitable for intravitreal injection. The composition can further include a stabilizer such as trehalose. The composition can also include a surfactant.

The biologic therapeutic agent is preferably an antibody. In a highly preferred embodiment, the biologic therapeutic agent is an IgG1/lambda isotype antibody and/or an isolated monoclonal antibody that specifically binds to a C5 protein.

In a preferred embodiment:

R1 is nothing, $CH_3$, $C_nH_{2n+1}$, $C_nH_{2n}$, or $C_nH_{2n-1}$ (n=1–10); and R2 includes an amine group, an amino group, an amido group, a methoxy group, an alkoxy group, an ester, an ether, a carboxylic acid or a combination thereof.

In a further preferred embodiment:

R1 is nothing, $CH_3$, $C_nH_{2n+1}$, $C_nH_{2n}$, or $C_nH_{2n-1}$ (n=1–10); and R2 includes an amine group and a carboxylic acid group.

In a still further preferred embodiment:

R1 is a $C_1$-$C_9$ alkyl group, more preferably a $C_1$-$C_5$ alkyl group and even more preferably a $C_2$-$C_4$ alkyl group; and R2 is $NH_2COOH$, $NH_2CH_2CH_2SO_3H$ or a combination thereof.

In a still further preferred embodiment:

R1 is a $C_1$-$C_9$ alkyl group, more preferably a $C_1$-$C_5$ alkyl group and even more preferably a $C_2$-$C_4$ alkyl group; and R2 is $NH_2COOH$.

In a highly preferred embodiment, the guanidine derivative is arginine, particularly L-arginine.

The composition, when containing the biologic at a concentration of 100 mg/ml, exhibits a viscosity that is at least 3 centipoise (cp), more typically at least 5 cp, even more typically at least 7 cp greater than a viscosity of a substantially identical composition that does not contain the biologic.

The composition, when containing the guanidine and/or guanidine derivative at a concentration of 50 mM, will typically exhibit a viscosity that is at least 3 centipoise (cp), more typically at least 5 cp, even more typically at least 7 cp lower than a viscosity of a substantially identical composition that does not contain the guanidine and/or guanidine derivative.

The biologic therapeutic agent has a molecular weight that is at least 25,000 daltons, more typically at least 50,000 daltons and even possibly at least 75,000 daltons, but no greater than 500,000 daltons, more typically no greater than 200,000 daltons and even possibly no greater than 125,000 daltons.

This present invention is also directed to an injection containing an aqueous composition as in any of the embodiments described herein. The injection an injection device wherein the injection device includes a chamber defining an a containment space and a needle defining a tunnel and wherein the tunnel is in fluid communication with the containment space and wherein the needle has a gauge of at least 25. The aqueous composition of any of the embodiments described herein is disposed in the containment space of the chamber. The composition in the containment space preferably has a volume that is at least 10 milliliters (ml), more typically at least 16 ml and even more typically at least 18 ml, but is typically no greater than 30 ml, more typically no greater than 24 ml and even more typically no greater than 22 ml.

The present invention is also directed to a method of injecting an aqueous pharmaceutical composition of any of the embodiments described herein. The method includes the steps of:

providing the injection as described herein;

piercing biological tissue of a biologic target with the needle; and injecting the composition into the biologic target.

Preferably, the biologic tissue is the cornea, the sclera, the conjunctiva or a combination thereof, the biologic target is the eye, and the step of injecting the composition includes injecting the composition into the vitreous of the eye.

BRIEF DESCRIPTION OF THE DRAWINGS

FIG. 1 is a chart showing aggregation of a biologic in various different compositions.

DETAILED DESCRIPTION OF THE INVENTION

The present invention is predicated upon the formation of a pharmaceutical composition, preferably an ophthalmic composition, that is suitable for injection into a mammal, particularly a human body and preferably suitable for intravitreal injection into the vitreous of a mammalian eye, particularly the human eye. In a narrow sense, the invention involves the discovery that low concentrations of arginine, particularly L-arginine, do not exhibit any significant toxicity to the eye while still maintaining the ability to sufficiently lower the viscosity of an aqueous composition containing an IgG1/lambda isotype monoclonal antibody thereby making that aqueous composition suitable for intravitreal injection. In a broader sense, it is contemplated that the invention of the present application could be applied to other monoclonal antibodies or other antibodies or biologic therapeutic agents (i.e., biologics) in general. It is further contemplated that guanidine and guanidine derivatives other than arginine may also be used at low concentrations to lower viscosity of aqueous composition containing IgG1/lambda isotype monoclonal antibody or other such antibodies or biologics. While the composition of the present invention has been found particularly desirable for intravitreal injection, it is further contemplated that compositions can be formed hereunder for application to other biological targets (e.g., intramuscular injections or the like) of the body if the toxicity of the guanidine and/or guanidine derivative, particularly arginine, proves sufficiently low relative to that biological target. Advantageously, the discoveries discussed herein open pathways of delivery of not only the antibodies discussed herein, but potentially other biologics as well.

The biologic of the composition of the present application is preferably a binding antibody or antigen binding fragment. The biologic is typically present in the composition at a concentration that is at least 10 milligrams per milliliter (mg/ml), more typically at least 50 mg/ml, even more typically at least 75 mg/ml and still more typically at least 90 mg/ml. The biologic is also typically present in the composition at a concentration that is no greater than 200 milligrams per milliliter (mg/ml), more typically no greater than 150 mg/ml, even more typically no greater than 125 mg/ml and still more typically no greater than 110 mg/ml. Compositions of the present invention containing the biologic, at these concentrations, and particularly at a concentration of 100 mg/ml, will typically exhibit a viscosity that is at least 3 centipoise (cp), more typically at least 5 cp, even more typically at least 7 cp greater than a viscosity of a substantially identical composition that does not contain the biologic. As used herein, a substantially identical composition that does not contain the biologic is a composition having exactly the same concentrations of each of the excipients of the composition of the present invention with the exception that the biologic is not present. For this definition of substantially identical composition, water is not considered an excipient, but is present in the substantially identical composition in an amount sufficient that the excipients are at proper concentrations. Example 2 of the examples presented below illustrates such a substantially identical composition. Furthermore, compositions containing only the biologic at these concentrations in water, and particularly at a concentration of 100 mg/mL, will typically having a viscosity that is at least 10 cp, more typically at least 15 cp and even possibly at least 20 or even 22 cp.

Unless otherwise specifically stated, viscosity of any composition discussed herein is determined at a temperature of 20° C. and a shear rate of 1029 s$^{-1}$ with a cone spindle of geometry 0.50°/40 mm.

The biologic of the present invention typically has a molecular weight that is at least 25,000 daltons, more typically at least 50,000 daltons and even possibly at least 75,000 daltons. The biologic of the present invention also typically has a molecular weight that is no greater than 500,000 daltons, more typically no greater than 280,000 daltons and even possibly no greater than 175,000 daltons.

In a preferred embodiment, the biologic is an isolated complement C5-binding molecule (e.g., C5-binding antibody or antigen binding fragment thereof). The biologic can be an isolated antibody or antigen binding fragment thereof that specifically binds to a C5 protein, wherein said antibody has an affinity constant ($K_A$) of at least $1\times10^7 M^{-1}$, $10^8 M^{-1}$, $10^9 M^{-1}$, $10^{10} M^{-1}$, or $10^{11} M^{-1}$. Additionally or alternatively, the biologic can be an isolated antibody or antigen binding fragment thereof that specifically binds to a C5 protein and inhibits the alternative complete pathway as measured by in vitro hemolytic assay with an $IC_{50}$ range from about 20 pM to about 200 pM.

In a preferred embodiment, the antibody of the invention is an isolated monoclonal antibody that specifically binds to a C5 protein. The antibody can be an isolated human or humanized monoclonal antibody that specifically binds to a C5 protein. The antibody can additionally or alternatively be an isolated chimeric antibody that specifically binds to a C5 protein. As a further additional or alternative characteristic, the antibody can comprise a human heavy chain constant region and a human light chain constant region.

The antibody can be a single chain antibody that specifically binds to a C5 protein. The antibody can be a Fab fragment. The antibody can additionally or alternatively be scFv. Preferably, the antibody is an IgG isotype.

It is also contemplated that the isolated antibody or antigen binding fragment thereof can comprise a framework in which amino acids have been substituted into the antibody framework from respective human VH or VL germline sequences.

The biologic can include vectors and host cells comprising nucleic acids. In one embodiment, the biologic comprises one or more isolated host cells that include, without limitation, (1) a recombinant DNA segment encoding a heavy chain of the antibodies of the invention, and (2) a second recombinant DNA segment encoding a light chain of the antibody of the invention; wherein said DNA segments are respectively operably linked to a first and a second promoter, and are capable of being expressed in said host cell. In another embodiment, the biologic can include isolated host cells comprising a recombinant DNA segment encoding a heavy chain, and a light chain of the antibody, respectively, wherein said DNA segment is operably linked to a promoter, and is capable of being expressed in said host cells. In some embodiments, the host cells are non-human mammalian cell line. In some embodiments, the antibodies or antigen binding fragments thereof are a human monoclonal antibody, or an antigen binding fragment thereof.

Examples of desirable monoclonal antibodies or antigen binding fragments thereof that specifically binds to a C5 protein are disclosed in U.S. Patent Application No. 20100034809, which is incorporated herein by reference for all purposes.

The composition of the present invention also includes guanidine, or a guanidine derivative (i.e., any molecule that includes a guanidinium group) or a combination thereof. This means that the composition can include guanidine only, guanidine derivative only or a combination of guanidine and guanidine derivative. The guanidine derivative is preferably according to the following formula:

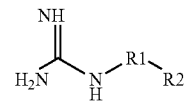

wherein:
R1 is nothing, $CH_3$, $C_nH_{2n+1}$, $C_nH_{2n}$, or $C_nH_{2-1}$ (n=1-10); and/or
R2 is nothing or any chemical group that does not significantly reduce the ability of the guanidinium group to lower the viscosity of the composition; and
R1 and R2 are never nothing at the same time.

As used herein, the phrase "does not significantly reduce the ability of the guanidinium group to lower the viscosity of the composition" means that, compared to a preselected amount of guanidine, an equivalent molar amount of the guanidine derivative lowers the viscosity of the composition at least 70% as much as the guanidine. In other words, if 2 moles of guanidine were provided in a composition and lowered the viscosity of the composition 10 cps relative to the composition without guanidine, then replacing the 2 moles of guanidine with 2 moles of guanidine derivative would lower the viscosity of the same composition at least 7 cps relative to the composition without guanidine or a guanidine derivative.

In a preferred embodiment:
R1 is nothing, $CH_3$, $C_nH_{2n+1}$, $C_nH_{2n}$, or $CH_2H_{2n-1}$ (n=1-10); and
R2 includes an amine group, an amino group, an amido group, a methoxy group, an alkoxy group, an ester, an ether, a carboxylic acid or a combination thereof.

In a further preferred embodiment:
R1 is nothing, $CH_3$, $C_nH_{2n+1}$, $C_nH_{2n}$, or $C_nH_{2n-1}$ (n=1-10); and
R2 includes an amine group and a carboxylic acid group.

In a still further preferred embodiment:
R1 is a $C_1$-$C_9$ alkyl group, more preferably a $C_1$-$C_5$ alkyl group and even more preferably a $C_2$-$C_4$ alkyl group; and
R2 is $NH_2COOH$, $NH_2CH_2CH_2SO_3H$ or a combination thereof.

In a still further preferred embodiment:
R1 is a $C_1$-$C_9$ alkyl group, more preferably a $C_1$-$C_5$ alkyl group and even more preferably a $C_2$-$C_4$ alkyl group; and
R2 is $NH_2COOH$.

It is also preferable that R1 is a straight chain alkyl group. Arginine, particularly L-arginine, is a highly preferred guanidine derivative for the composition and is also a guanidine derivative and an amino acid.

It has been suggested that arginine and compounds similar to arginine can be toxic. However, it has been advantageously found that lower levels of arginine exhibit substantially lower toxicity and even substantial non-toxicity. It has been specifically found that lower concentrations of arginine do not cause damage to photoreceptor cells of the eye of a rabbit while higher concentrations (e.g., about 150 mM) have shown damage to photoreceptor cells. As such, the guanidine and/or guanidine derivative, particularly arginine and more particularly L-arginine, is typically present in the composition at a concentration that is at least 25 mM, more typically at least 35 mM and even more typically at least 45 mM. The guanidine and/or guanidine derivative, particularly arginine and more particularly L-arginine, is also typically present in the composition at a concentration that no greater than 100 mM, more typically no greater than 65 mM and even more typically at least 55 mM.

Advantageously, the guanidine and/or guanidine derivative (e.g., L-arginine), even at the low concentrations recited above, can substantially reduce the viscosity of the composition produced by the inclusion of the biologic within the composition. Compositions of the present invention containing the guanidine and/or guanidine derivative, at the above concentrations, and particularly at a concentration of 50 mM, will typically exhibit a viscosity that is at least 3 centipoise (cp), more typically at least 5 cp, even more typically at least 7 cp lower than a viscosity of a substantially identical composition that does not contain the guanidine and/or guanidine derivative. As used herein, a substantially identical composition that does not contain the guanidine and/or guanidine derivative is a composition having exactly the same concentrations of each of the excipients and the biologic of the composition of the present invention with the exception that the guanidine and/or guanidine derivative is not present. For this definition of substantially identical composition, water is not considered an excipient, but is present in the substantially identical composition in an amount sufficient that the excipients and biologic are at proper concentrations. Example 3 of the examples presented below illustrates such a substantially identical composition.

The composition of the present invention will also typically include a protein stabilizing agent, although not necessarily required unless specifically stated. Examples of potential protein stabilizing agents include without limitation, mannitol, sodium chloride, glycine and trehalose. In a preferred embodiment, the protein stabilizing agent is or consists essentially of trehalose. When included, the protein stabilizing agent is typically present in the composition at a concentration that is at least 50 mM, more typically at least 80 mM and even more typically at least 110 mM. When included, the protein stabilizing agent is also typically present in the composition at a concentration that is no greater than 250 mM, more typically no greater than 175 mM and even more typically no greater than 130 mM.

The composition of the present invention will also typically include a surfactant, although not necessarily required unless specifically stated. The surfactant can include non-ionic, an anionic, a cationic, or an amphoteric or zwitterionic surfactant or a combination of such surfactants. Examples of potentially suitable surfactant include, without limitation, ethers of fatty alcohols and/or polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens®, polyoxyethylene stearates, polysorbates, polaxamers, cyclodextrins, combinations thereof or the like. Polysorbate 20 is a particularly preferred surfactant. When included, the surfactant is typically present in the composition at a concentration that is at least 0.001 w/v %, more typically at least 0.005 w/v % and even more typically at least 0.009 w/v %. When included, the protein stabilizing agent is also typically present in the composition at a concentration that is no greater than 0.1 w/v %, more typically no greater than 0.05 w/v % and even more typically no greater than 0.015 w/v %.

The composition of the present invention will also typically include a buffering agent, although not necessarily required unless specifically stated. Examples of potentially suitable buffering agents include, without limitation, sodium phosphate, citrate and histidine. Histidine is a particularly preferred buffering agent. When included, the buffering agent is typically present in the composition at a concentration that is at least 2 mM, more typically at least 7 mM and even more typically at least 9 mM. When included, the buffering agent is also typically present in the composition at a concentration that is no greater than 30 mM, more typically no greater than 15 mM and even more typically no greater than 11 mM.

Additional Ingredients

Various additional ingredients can be included in the composition of the present invention. The composition of the present invention are typically aqueous and typically include a substantial amount (e.g., at least 60 or 90 w/v %) of water.

As one particular advantage of the present invention, it has been found that guanidine and/or guanidine derivative, particularly arginine, can reduce aggregation of the biologic, particularly aggregation of an isolated monoclonal antibody that specifically binds to a C5 protein. It has also advantageously been found that the guanidine and/or guanidine derivative (e.g., L-arginine) and the biologic (e.g., an isolated monoclonal antibody that specifically binds to a C5 protein) can be combined in composition of the present invention to substantially lower the viscosity of the composition, particularly at lower pH. The viscosity of the composition is typically at least 2 cp, more typically at least 3 cp and even more typically at least 4 cp. The viscosity of the composition is also typically no greater than 10 cp, more typically no greater than 7.5 cp and even more typically no greater than 6 cp or even 5.5 cp. The pH of the composition is typically at least 3, more typically at least 4 and even more typically at least 5.2. The viscosity of the composition is also typically no greater than 8, more typically no greater than 6.5 and even more typically no greater than 5.9 or even 5.7.

By providing such lowered viscosity, the composition can be administered much easier through an injection device and particularly through a relatively small gauge needle. As used herein, the term "small gauge needle" refers to any elongated tubular member designed to penetrate and be inserted through biologic tissue such as skin or ocular tissue (e.g., corneal, scleral and/or conjunctival tissue). Further, the term "gauge", as used herein, is meant to provide referrals to inner and outer diameters of the common numerical gauge system used for syringe needles. Advantageously, compositions of the present invention can be injected through small gauge needles having a gauge that is at least 27, more typically at least 28, still more typically at least 29 or 30 and even possibly at least 31. As a further advantage, the ability to use such small gauge needles allows for more desirable intravitreal injection of composition of the present invention for treatment of retinal diseases such as age related macular degeneration.

Thus, the present invention is further directed to methods of treating diseases. Accordingly, an injection device (e.g., a syringe) having a chamber defining a containment space that is in fluid communication with a tunnel of a small gage needle is typically provided. The containment space is loaded or otherwise filled with the composition of the present invention. The injection device can then be used to deliver the composition to a biological target. Preferably, the small gauge needle is used to pierce the tissue of the biologic target followed by injection of the composition to the target. As suggested, the composition allows for particularly suitable injection to the eye. Thus, in a preferred embodiment the biologic target is the eye, the tissue pierced by the needle is the cornea, the conjunctiva, the sclera or a combination thereof and the composition is injection into the vitreous of the eye.

The volume of the injection is typically is typically at least 10 microliters (μl), more typically at least 35 μl and even more typically at least 45 μl. The volume of the injection is also typically no greater than 100 μl, more typically no greater than 75 μl and even more typically no greater than 60 μl.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

EXAMPLES

Example 1

Table 1 above is a formulation for one exemplary emulsion in accordance with the present invention.

TABLE 1

| COMPONENT | CONCENTRATION |
| --- | --- |
| Biologic (e.g., an isolated monoclonal antibody that specifically binds to a C5 protein) | 100 mg/mL |
| Stabilizer (e.g., trehalose) | 120 mM |
| Guanidine and/or guanidine derivative (e.g., L-arginine) | 50 mM |
| Histidine | 10 mM |
| Surfactant | 0.01 w/w % |
| Sodium Hydroxide | Adjust pH to 5.5 |
| Hydrochloric Acid | Adjust pH to 5.5 |
| Purified Water | QS 100 |

It is understood that the concentrations in table I can be varied by ±10%, ±20%, ±30%, ±90% of those concentrations or more and that those variances can be specifically used to create ranges for the ingredients of the composition of the present invention. For example, an ingredient at a concentration of 10 mM with a variance of ±20% means that the ingredient can have a concentration range of 8 to 12 mM.

Example 2

As discussed above, compositions of the present invention containing a biologic at particular concentrations will exhibit a viscosity that is greater than a viscosity of a substantially identical composition that does not contain the biologic. For exemplary purposes, Table 2 below shows a composition according to the present invention and a substantially identical composition that does not contain the biologic.

TABLE 2

| Ingredients | Formulation of Invention | Substantially Identical Formulation |
| --- | --- | --- |
| Biologic | 100 mg/ml | 0.000 mg/ml |
| Arginine | 10.5 mg/ml | 10.5 mg/ml |
| Polysorbate | 0.1 mg/ml | 0.1 mg/ml |
| NaOH | 0.5 mg/ml | 0.5 mg/ml |
| Trehalose | 45.4 mg/ml | 45.4 mg/ml |
| water | Q.S. to 1 ml | Q.S. to 1 ml |

Example 3

As discussed above, compositions of the present invention containing an guanidine and/or guanidine derivative at particular concentrations will exhibit a viscosity that is lower than a viscosity of a substantially identical composition that does not contain the guanidine and/or guanidine derivative. For exemplary purposes, Table 3 below shows a composition according to the present invention and a substantially identical composition that does not contain the guanidine and/or guanidine derivative.

TABLE 3

| Ingredients | Formulation of Invention | Substantially Identical Formulation |
| --- | --- | --- |
| Biologic | 100 mg/ml | 100 mg/ml |
| Arginine | 10.5 mg/ml | 0.0 mg/ml |
| Polysorbate | 0.1 mg/ml | 0.1 mg/ml |
| NaOH | 0.5 mg/ml | 0.5 mg/ml |
| Trehalose | 45.4 mg/ml | 45.4 mg/ml |
| water | Q.S. to 1 ml | Q.S. to 1 ml |

Example 4

Table 4 below is provided to illustrate the effect of relatively low concentrations of the guanidine and/or guanidine derivative, L-arginine, on formulation containing a biologic in accordance with the present invention. The particular biologic in formulations 1 through 13 of table 4 is an isolated monoclonal antibody that specifically binds to a C5 protein.

| Formulation | Histidine Buffer (mM) | Stabilizer | Stabilizer conc. (mM) | Additional arginine conc. (mM) | Polysorbate 20 (%) | Color | Measured pH | Viscosity (mPas) | Osmolality (mOsm/kg) |
|---|---|---|---|---|---|---|---|---|---|
| 01 | 10 | Trehalose | 170 | — | 0.01 | Colorless | 5.5 | 13.1 | 247 |
| 02 | 10 | Arginine | 150 | — | 0.01 | Colorless | 5.4 | 3.2 | 305 |
| 03 | 10 | Trehalose | 120 | 50 | 0.01 | Colorless | 5.5 | 5.1 | 274 |
| 04 | 10 | Trehalose | 170 | — | 0 | Colorless | 5.4 | 10.6 | 257 |
| 05 | 10 | Arginine | 150 | — | 0 | Colorless | 5.5 | 3.5 | 308 |
| 06 | 10 | Trehalose | 120 | 50 | 0 | Colorless | 5.5 | 5.3 | 280 |
| 07 | 20 | Trehalose | 170 | — | 0.01 | Colorless | 5.5 | 11.9 | 278 |

As can be seen, even relatively low concentrations of arginine can significantly lower the viscosity of the compositions containing the biologic. As suggested, guanidine and/or guanidine derivative and particularly arginine can lower the aggregation of the biologic. With reference to FIG. 1, it can be seen that the formulations with arginine (i.e., formulations 2, 3, 5, 6, 9, 10, 12 and 13) exhibit significantly reduced aggregation. For FIG. 1, t=0 is time equal to zero, shaking is measurement after shaking, F/T is measurement after freeze/thaw cycle and 40° C. 6 w is measurement after six weeks of storage at 40° C.

Comparative Data

Table 5 below present comparative data showing the ability of guanidine and guanidine derivatives to reduce the viscosity of the biologic relative to the ability of other chemical entities that have been used in the prior art for reducing viscosity.

TABLE 5

| Sample ID | LFG316 | Buffer/Excipient | Turbidity (75M) | Viscosity (mPa · s) |
|---|---|---|---|---|
| DS/Active formulations | | | | |
| Formula 1 | 100 mg/mL | Histidine 10 mM, PS20 0.01%(w/v), Trehalose 170 mM | 22.3 | 19.77 |
| Formula 2 | 100 mg/mL | Histidine 10 mM, PS20 0.01%(w/v), Arginine 150 mM | 30.8 | 3.64 |
| Formula 3 | 100 mg/mL | Histidine 10 mM, PS20 0.01%(w/v), Guanidine 150 mM | 43.4 | 3.80 |
| Formula 4 | 100 mg/mL | Histidine 10 mM, PS20 0.01%(w/v), Urea 150 mM | 24.6 | 14.98 |
| Formula 5 | 100 mg/mL | Histidine 10 mM, PS20 0.01%(w/v), Taurin 150 mM | 22.6 | 14.95 |

As can be seen, arginine and guanidine were far superior in reducing the viscosity of the biologic (i.e., an IgG1/lambda isotype monoclonal antibody) relative to trehalose, urea and taurin.

Toxicity Data

A study was performed to determine the toxicity of an Arginine-containing formulation buffer following intravitreal administration to the New Zealand White rabbit for 4 weeks. Three buffers in 50 µl volumes and varying in concentrations of Arginine were injected intravitreally on a weekly basis for 3 weeks (i.e., three doses) and evaluated for toxicity. The three buffers were as follows: (1) 10 mM Histidine, 170 mM Trehalose, 0.01% polysorbate 20, pH 5.5; (2) 50 mM Arginine, 10 mM Histidine, 120 mM Trehalose, 0.01% polysorbate 20, pH 5.5; and (3) 150 mM Arginine, 10 mM Histidine, 0.01% polysorbate). The buffer containing 150 mM Arginine showed degeneration/atrophy of the retina either bilaterally or unilaterally in 4 out of 6 animals. Minimal changes were characterized by a focal to multifocal loss of the photoreceptors layer whereas in more severe cases, other layers were affected, resulting in atrophy of the retina. Intravitreal administration of the buffer containing 50 mM arginine was very well tolerated and gave no indication of ocular toxicity.

A study was performed in which the following formulation: an antibody, 50 mM Arginine; 10 mM Histidine; 120 mM Trehalose, 0.01% polysorbate 20, pH 5.5, was administered intravitreally to cynomolgus monkeys for at least 26 weeks. The formulation was administered in both eyes (50 µL/eye) once every two weeks for 26 weeks (14 doses). Based on the results of this study, intravitreal administration of the formulation at repeated dosing up to 5 mg/eye to the cynomolgus monkey was very well tolerated and gave no indication of test item toxicity.

We claim:

1. An aqueous composition suitable for injection, comprising:
   at least 50 mg/ml of a biologic therapeutic agent;
   guanidine and/or guanidine derivative, wherein the guanidine derivative is arginine; and
   wherein the guanidine and/or guanidine derivative is present in the composition at a concentration of at least 25 mM but no greater than 100 mM; and
   water;
   wherein the composition has a viscosity that is no greater than 10 centipoise, and
   wherein the biologic therapeutic agent is an isolated monoclonal antibody that specifically binds to a C5 protein, and
   wherein the composition is an aqueous ophthalmic composition suitable for intravitreal injection.

2. A composition as in claim 1 further comprising a stabilizer.

3. A composition as in claim 2 wherein stabilizer is trehalose.

4. A composition as in claim 1 further comprising a surfactant.

5. A composition as in claim 1 wherein the viscosity of the composition is no greater than 7 centipoise.

6. A composition as in claim 1 wherein the guanidine and/or guanidine derivative is L-arginine.

7. A composition as in claim 1 wherein the composition, when containing the biologic therapeutic agent at a concentration of 100 mg/ml, exhibits a viscosity that is at least 3 centipoise greater than a viscosity of a substantially identical composition that does not contain the biologic therapeutic agent.

8. A composition as in claim 1 wherein the composition, when containing the guanidine and/or guanidine derivative at a concentration of 50 mM, exhibits a viscosity that is at least 7 cp lower than a viscosity of a substantially identical composition that does not contain the guanidine and/or guanidine derivative.

9. A composition as in claim 1 wherein the biologic therapeutic agent has a molecular weight that is at least 25,000 daltons, but no greater than 500,000.

10. A composition as in claim 1 wherein the biologic therapeutic agent has a molecular weight that is at least 75,000 daltons, but no greater than 125,000.

11. An injection containing an aqueous ophthalmic composition, the injection comprising:

an injection device wherein the injection device includes a chamber defining a containment space and a needle defining a tunnel and wherein the tunnel is in fluid communication with the containment space and wherein the needle has a gauge of at least 25;

an aqueous ophthalmic composition disposed in the containment space of the chamber, the aqueous ophthalmic composition comprising:

i. at least 50 mg/ml of a biologic therapeutic agent, wherein the biologic therapeutic agent is an isolated monoclonal antibody that specifically binds to a C5 protein;

ii. guanidine and/or guanidine derivative, wherein the guanidine derivative is arginine;and
wherein the guanidine and/or guanidine derivative is present in the composition at a concentration of at least 25 mM but no greater than 100 mM; and iii. water;

wherein the viscosity of the composition is no greater than 7 centipoise and wherein the composition, when containing the biologic therapeutic agent at a concentration of 100 mg/ml, exhibits a viscosity that is at least 7 cp greater than a viscosity of a substantially identical composition that does not contain the biologic therapeutic agent and wherein the composition, when containing the guanidine and/or guanidine derivative at a concentration of 50 mM, exhibits a viscosity that is at least 7 cp lower than a viscosity of a substantially identical composition that does not contain the guanidine and/or guanidine derivative and wherein the biologic therapeutic agent has a molecular weight that is at least 50,000 daltons but no greater than 200,000 daltons and wherein the composition in the containment space has a volume that is at least 16 ml, but no greater than 24 ml.

12. An injection as in claim 11 wherein the biologic therapeutic agent is an IgG1/lambda isotype antibody and the guanidine and/or guanidine derivative is L-arginine.

13. A method of injecting an aqueous pharmaceutical composition, the method comprising:
providing the injection of claim 12;
piercing biological tissue of a biologic target with the needle wherein the biologic target is an eye having a vitreous and the biologic tissue is the cornea, the sclera, the conjunctiva or a combination thereof, the biologic target is the eye; and
injecting the composition into the vitreous.

* * * * *